United States Patent
Huettmann et al.

(10) Patent No.: US 7,961,333 B2
(45) Date of Patent: Jun. 14, 2011

(54) METHOD FOR SCANNING OPTICAL INTERFERENCE PATTERNS WITH LINE SENSORS

(75) Inventors: Gereon Huettmann, Luebeck (DE); Peter Koch, Luebeck (DE)

(73) Assignee: Universitaet Zu Luebeck, Luebeck (DE)

( * ) Notice: Subject to any disclaimer, the term of this patent is extended or adjusted under 35 U.S.C. 154(b) by 149 days.

(21) Appl. No.: 12/307,808

(22) PCT Filed: Jul. 4, 2007

(86) PCT No.: PCT/DE2007/001179
§ 371 (c)(1),
(2), (4) Date: Sep. 9, 2009

(87) PCT Pub. No.: WO2008/003302
PCT Pub. Date: Jan. 10, 2008

(65) Prior Publication Data
US 2010/0020328 A1   Jan. 28, 2010

(30) Foreign Application Priority Data
Jul. 7, 2006   (DE) .................. 10 2006 031 822

(51) Int. Cl.
*G01B 9/02* (2006.01)
*G01B 11/02* (2006.01)
(52) U.S. Cl. ....................... 356/499; 356/521
(58) Field of Classification Search .......... 356/488, 356/494, 499, 521
See application file for complete search history.

(56) References Cited

U.S. PATENT DOCUMENTS
5,943,133 A * 8/1999 Zeylikovich et al. ......... 356/496

FOREIGN PATENT DOCUMENTS
DE   196 15 616   10/1997
EP   0 930 485   7/1999

OTHER PUBLICATIONS

Koch et al., "Optical Coherence Tomography System with Extended Measurement Range", Optics Letters, Optical Society of America, vol. 31, No. 19, Oct. 1, 2006, pp. 2882-2884.

* cited by examiner

*Primary Examiner* — Patrick J Connolly
(74) *Attorney, Agent, or Firm* — Diederiks & Whitelaw, PLC

(57) ABSTRACT

A method is provided for the electronic scanning of the intensity distribution of an optical interference pattern by means of a linear image sensor, wherein the interference pattern is produced by overlapping two temporally partly coherent beams striking at an arbitrarily predefined angle $\alpha$ in relation to one another and is provided with an interference strip having a carrier frequency greater than the scanning frequency, and amplitude modulation that can be varied slowly in relation to the pixel width, wherein at least one optical grating is disposed in the beam path of at least one of two incident beams and the image sensor is disposed in the diffraction image of the grating(s) such that, at the site of the image sensor, the beams interfere, and the beams enclose an angle $\beta$ at the site of the image sensor, the angle being smaller than $\alpha$.

14 Claims, 3 Drawing Sheets

METHOD FOR SCANNING OPTICAL INTERFERENCE PATTERNS WITH LINE SENSORS

CROSS-REFERENCE TO RELATED APPLICATIONS

This application represents a National Stage application of PCT/DE2007/001179 entitled "Method for Scanning Optical Interference Patterns by Means of Line Sensors" filed Jul. 4, 2007, pending.

BACKGROUND OF THE INVENTION

The invention relates to a method for scanning optical interference patterns with line sensors according to the preamble of the main claim. In particular, a description is given of a method for scanning optical interference patterns arising on superimposing two time partly coherent, non-parallel light beams on a linear image sensor.

An example of a linear image sensor is a line sensor comprising linear juxtaposed, light-sensitive pixels, which can be electronically read in order to detect an interference pattern with a measuring device, e.g. a PC. A linear image sensor can also comprise several juxtaposed pixel lines. In exemplified manner hereinafter reference is simply made to line sensors.

Such scanning processes for optical interference signals are of a standard nature in optical coherence tomography (OCT), particularly when carried out without movable components, as is e.g. described in WO 2002/084263 A1. It is also known that the scanning depth of such a "NoMotion-OCT" a priori is very limited compared with other OCT methods, where scanning depths of a few millimeters are obtained.

In order to obtain a comparable scanning depth, it is e.g. possible to place a so-called stepped mirror, which reflects components of the reference beam with different path lengths, in place of a mirror in the reference arm of a Michelson interferometer. Such a mirror, which must have step heights in the micrometer range, is far from easy to manufacture.

The solution of DE 196 15 616 A1 is simpler in practice and therein the reference arm mirror is replaced by a tilted reflection grating. This leads to reflections in the directions of the diffraction orders of the grating and one of said reflected beams is deflected onto the detector. Using beam optics (lens), placed in the diffraction pattern of the grating, in the solid angle range of a selected diffraction order, the individual grooves are imaged on different pixels of the detector in order to obtain a pixel-ordered transit time distribution of the reference light beam. Thus, the detector is no longer in the diffraction pattern and in particular imaging cancels out the divergence of different spectral components by grating diffraction on the detector. According to DE 196 15 616 A1, the grating is only partly in the focal plane of the beam optics, so that imaging is not equally successful on all the pixels, which gives rise to additional evaluation problems.

In the test assembly of U.S. Pat. No. 5,943,133 said problem is obviated, because the reflection grating, focal plane and detector are precisely parallel. The measurement and reference light beams are diffracted by means of the same grating in such a way that reflections of both beams impinge on the detector substantially parallel with different diffraction orders. Here again an image and not the diffraction pattern of the grating is detected on the detector. The imaging of the grating on the detector is used for the practical implementation of a stepped mirror from which is obtained a clearly defined transit time distribution on the detector pixels. Through the simultaneous reflection of measurement and reference light said virtual stepped mirror has twice the step height compared with DE 196 15 616 A1.

However, the precise imaging of the finally structured grating (structural sizes of a few millimeters have to be resolved) makes high demands on the beam optics and account must also be taken in the evaluation of aberrations as a further error source.

In other test assemblies, such as e.g. according to WO 2002/084263 A1, there is no need for imaging optics. Normally here there is only a beam focussing perpendicular to the sensor line, e.g. with a cylindrical lens, in order to obtain an intensity rise for the measurement light on the detector. This gives rise to no evaluation problems.

In the structure of WO 2002/084263 A1 the scanning depth can be particularly easily increased, in that on superimposing on the line sensor the reference beam can be tilted against the specimen beam. However, this leads to a finer spatial structure of the amount of the electrical field and therefore the light intensity distribution directly at the detector. Thus, there are far more interference fringes on the same detector surface. Normally there are more interference fringes per pixel. However, for scanning a sine wave train the scanning theorem requires at least two scans per full wave. The underscanning of the interference signal is very unfavourable with line sensors, because they can only measure in integrating manner over pixel surfaces, so that it is not readily possible to reconstruct an underscanned signal. Underscanning must be avoided for appropriate evaluation.

Hitherto there has been no technically readily practicable solution of the scanning problem with respect to a sensor having a higher pixel density (approximately 10,000 pixels), because it is expensive to manufacture and can only be read with difficulty. Standard line sensors have approximately 1,000 pixels.

DE 10 2004 033 187 B3 discloses an easy way out for the case where interest is only attached to the mean course of an intensity amplitude distribution as opposed to the detection of the complete interference pattern. This is the true measurement function of the OCT. The optical interference signal appears as an amplitude-modulated, rapidly oscillating intensity distribution along the sensor line and the specimen information is carried not by the interference fringes, but their envelope. The term oscillation here means a time-stationary carrier frequency measured as the reciprocal length on the image sensor.

In the case of the OCT, where short-coherent light is used, the envelope is a convolution of the coherence function with an interference signal, which arises through transit time distribution in the specimen. The coherence function is determined once and for all for a light source and then it is possible to calculate the transit time distribution from the envelope. Thus, DE 10 2004 033 187 B3 proposes to avoid the underscanning of the interference pattern by a suitable masking of the line sensor. The periodic mask to be used multiplies the interference signal in such a way that slowly oscillating components arise, which can be readily scanned with the given pixel resolution. Using telecommunications engineering language, mixing takes place on a low frequency intermediate band. However, the disadvantage of this measure is that considerable components of the already weak useful light with specimen information scattered back by the specimen are blocked out by the mixing process.

It is assumed hereinafter that on the line sensor is obtained an interference pattern by superimposing two time partly coherent, non-parallel, incident light beams, which can not be completely scanned according to the Nyquist condition with the given sensor pixel density. The interference pattern is essentially characterized by a carrier frequency (expressed as the number of interference fringes per pixel) and an amplitude modulation. It is assumed that the amplitude modulation is more slowly variable compared with the carrier wave, particularly approximately constant over a single pixel width. The latter is fundamentally not a restriction, because this is the case with any practical test assembly. It is left open as to the significance of amplitude modulation in each individual case.

SUMMARY OF THE INVENTION

The problem of the invention is to provide a method with which the amplitude modulation of an optical interference signal can be readily detected under the indicated prerequisites using the line sensor and without any underscanning occurring (below the Nyquist frequency).

The inventive method comprises the diffraction of at least one of the two light beams originally made to interfere on a grating introduced into the optical path. This can involve a transmission or a reflection grating. If one of the beams is not diffracted at a grating, it is referred to hereinafter as a light beam of the zero diffraction order impinging on the line sensor.

The at least one group of beams of the at least one diffracted beam emanating from the grating is obtained by constructive interference at the grating. The beams within a group pass out of the grating under different angles in accordance with the different diffraction orders.

Preferably a wavelength-dependent splitting of the at least one diffracted light beam is allowed and is not compensated by an imaging optics. The grating is not imaged on the detector. The detector is to be placed at a distance behind the grating which allows interference of elementary waves emanating from all the illuminated grooves on the detector, i.e. the detector is to be in the grating diffraction pattern.

BRIEF DESCRIPTION OF THE DRAWINGS

The invention is described hereinafter relative to the drawings, wherein show.

DETAILED DESCRIPTION OF THE INVENTION

Figure 1:
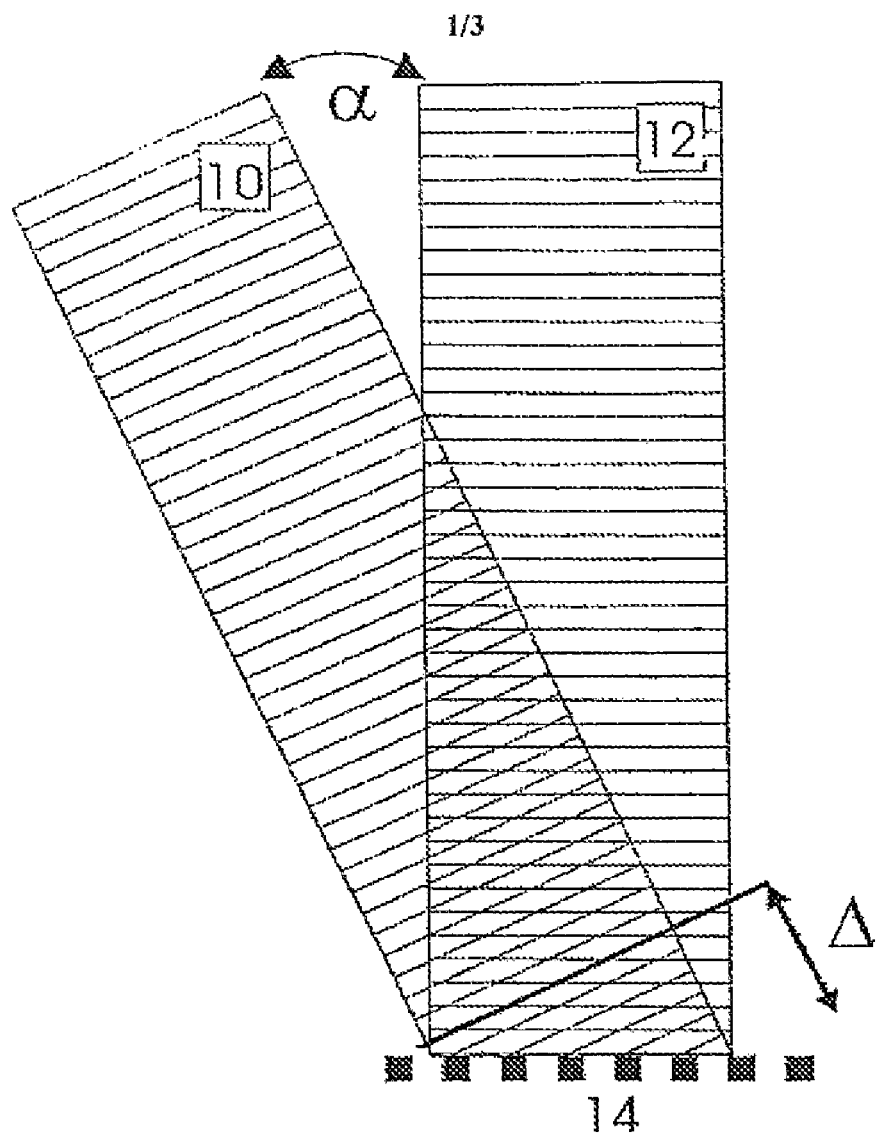
FIG. 1 Diagrammatically the transit time or path length difference resulting from the tilting of the irradiation directions.

FIG. 1 makes it clear that the angle $\alpha$ between the light beams directly influences the transit time distribution of the light on the sensor line. The left-impinging light beam 10 reaches the left-hand end of the detector 14 much earlier than the right, so that along the line sensor 14 the path length difference $\Delta$ for the beam 10 is set in a fixed manner. The perpendicular-impinging beam 12, however, has no transit time difference in the sensor plane. The interference fringes result directly from the spatial structure of the intensity of the superimposed electric field upstream of the sensor 14, which is clearly determined by the angle $\alpha$ between the wave fronts shown.

It is immediately clear that a decrease of this angle (towards zero) would reduce the interference signal carrier frequency and solve the scanning problem. The path length difference $\Delta$ along the sensor line 14, which corresponds to the scanning depth in the OCT, obtained as a result of tilting would, however, be correspondingly reduced.

Figure 2:
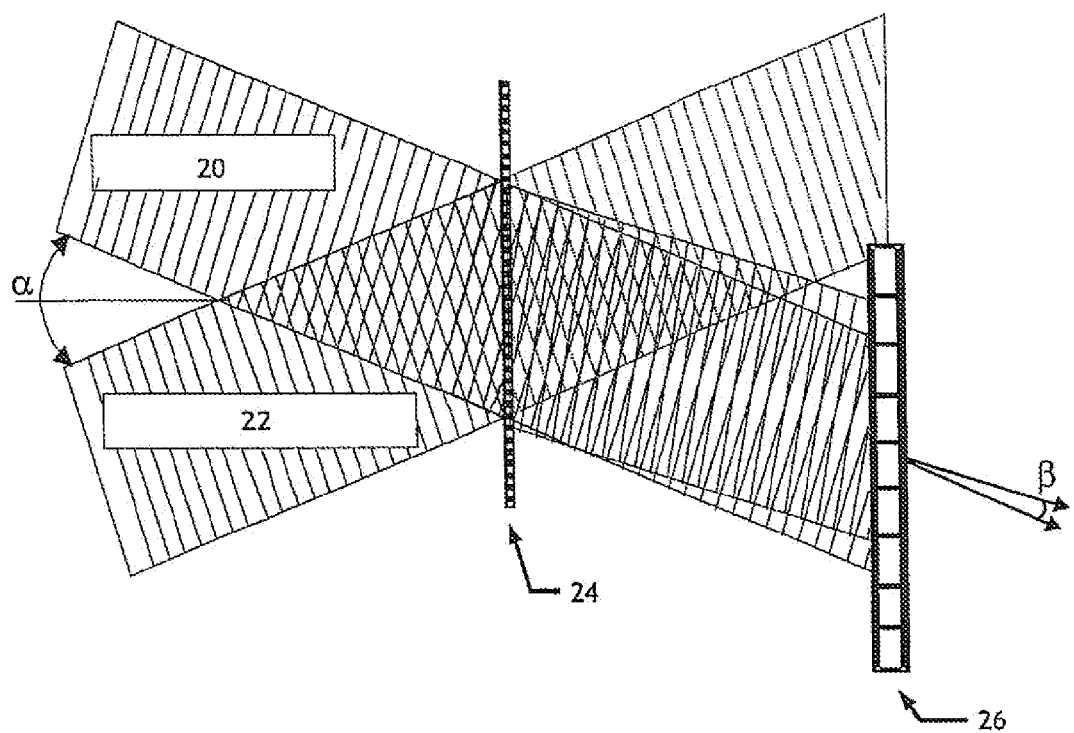
FIG. 2 The effect of the invention whereby the effective carrier frequency of the interference signal is significantly reduced.

FIG. 2 shows the possibility of an inventive solution, where two beams 20 and 22 are passed through the same grating 24 under incidence angles $\beta S$ and $\beta R$ and diffracted thereon. Different diffraction orders of the two beams 20 and 22 interfere on detector 26, the beams striking the detector behind the grating 24 now including a much smaller angle. The decisive point of the invention is the direction change of at least one of the two light beams due to grating diffraction. The other can be led past the grating or the zero diffraction order can be used.

In the case of grating diffraction a large number of elementary beams arising at the individual grating lines interfere. Under the constructional interference condition that the elementary waves have with respect to one another transit time differences representing integral multiples of wavelengths, a beam group under different diffraction orders and under different angles emanate from the grating. By definition, the beam at the zero diffraction order is parallel to the beam impinging on the grating and has no transit time difference of the elementary waves. The wave fronts of the nth diffraction order (n≠0, also: secondary diffraction order) comprise discreet n·λ displaced transit times, the total transit time difference being $\Delta = N \cdot n \cdot \lambda$ (N=number of contributing grating lines).

The inventively provided light deflection takes place by diffraction at the grating and not by reflection on a mirror or refraction on a prism. In the case of reflection on the mirror, the transmit times of all the beam components are identical and the intended effect of tilting the reference beam is cancelled out at the detector. At the prism the deflection results from the reduced speed of light in the medium and the condition that the positions of a wave front upstream or downstream of the prism are always characterized by the same optical path length covered.

Figure 3:
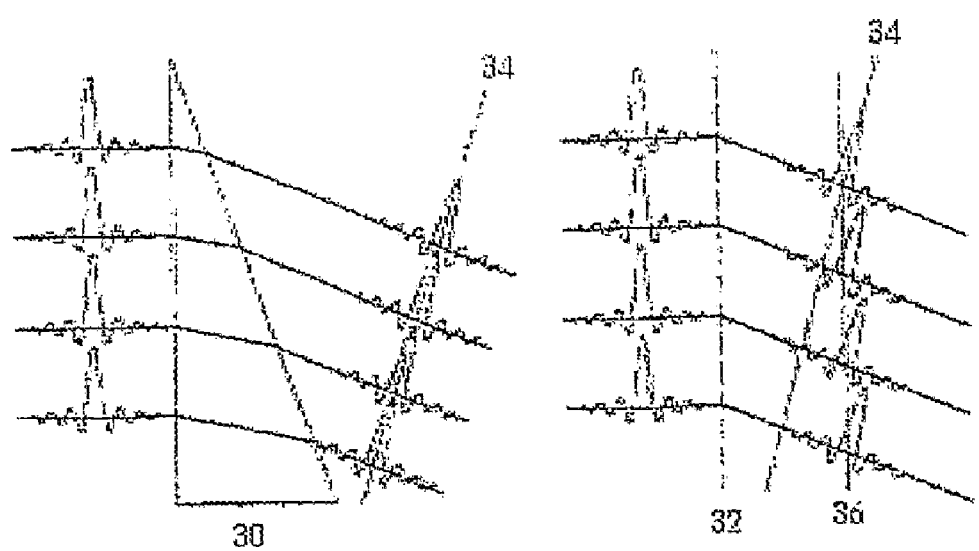
FIG. 3 The difference between the position of the wave front and the coherence location after traversing a prism (left) and a grating (right).

FIG. 3 shows in exemplified manner relative to the comparison of the light deflection by prism 30 and grating 32, how the position of the wave front 34 behaves with respect to the position of the coherence location 36 (in the left-hand image identical with 34). In particular, short-coherent light (intimated in the drawing) loses its beam-internal coherence in proportion to the deflection angle in the case of diffraction at the grating. This is utilized in the OCT on superimposing with the specimen beam, which has a scatter-depth-dependent transit time distribution in order to image the transit times on the detector pixel coordinates.

Short-coherent light, which comprises a wavelength spectrum, is deflected both by the prism and by the grating in wavelength-dependent manner. Thus, for the prism there is typically a nonlinear dispersion, so that the overall intensity distribution is disturbed. This disturbance cannot be readily, if at all, compensated during the evaluation of the recorded interference signals.

Grating diffraction produces by interference an achromatic phase displacement, which has no effects on the form of the amplitude modulation to be measured. This can be proved by an analytical calculation of the interference signal for broadband light with known spectral distribution, but this is not reproduced here.

From the formal standpoint, the two beams to be superimposed are characterized by wave number vectors k, whose values are dependent on the radiation wavelength and whose directions correspond to the irradiation directions (on the grating or detector). If one of the beams strikes a grating, the latter emits a set of beams with k-vectors, which within the individual beams differ by a reciprocal grating vector, i.e. only with respect to the parallel component relative to the grating orientation.

Thus, with the procedure according to the invention, in the diffraction pattern of the grating superimposing and measurement is to take place of those components of the two original beams on the detector where the difference of the parallel components of their k-vectors is minimal. The grating makes it possible to find the differences which are smaller than those of the original light beams impinging in tilted manner with respect to one another. The deflection of the beams at the grating does not cancel out the transit time distribution on the detector caused by the tilting, but does eliminate the scanning problem through the superimposing of virtually parallel phase fronts on the detector. The spectral divergence of the diffracted beams surprisingly has no influence on the amplitude modulation of the interference pattern produced with the diffracted beams. This represents the fundamental novelty resulting from the procedure according to the invention and the expert has hitherto been aware of this.

It is also not clear to the expert from the outset that through not imaging the grating on the detector (cf. DE 196 15 616 A1 and U.S. Pat. No. 5,943,133) no disadvantage with regards to the measurement occurs and instead it is possible to avoid expensive beam optics and the compensation of their errors during evaluation.

Normally the light source used is chosen in fixed form and its characteristics are well known. For performing the method used preferably two parameters are set in an appropriate manner, namely the angle between the two beams and/or the grating constant.

Preferably, for the case where one of the light beams has a low intensity from the outset (e.g. specimen beam in the OCT) no diffraction will take place and instead said first light beam is directly directed onto the detector (zero diffraction order). The second light beam will preferably be directed under such an angle to the first onto the grating that there is one of the secondary diffraction orders (typically the first order) of the resulting beam set under a small angle (around zero) with respect to the first light beam on the detector (cf. FIG. 2).

Alternatively or also additionally the grating constant can be appropriately chosen in such a way that the predetermined angle under which the two light beams were originally intended to strike the detector, corresponds precisely to the emergence angle of a higher diffraction order for the central wavelength of the light source. This grating constant can be chosen in elementary manner according to the known grating interference rules. Preferably use is made of phase gratings in order not to lose light intensity.

Unlike in the method of DE 10 2004 033 187 B3, the present invention is a manipulation of the light remote from the position of interference on the detector. In particular, the possibility is provided of leaving unchanged one of the two beams made to interfere, preferably the specimen beam for the OCT, which is impossible with detector masking.

The grating must be at an adequate distance from the detector, so that the elementary waves from all the illuminated grooves can interfere with one another on the detector. This distance should be in the millimeter scale magnitude (beam diameter×grating line spacing)/(2×central wavelength). As the grating-detector spacing or distance a few wavelengths, i.e. micrometers would not be adequate for the purposes of the invention, because then it would not be possible to assume a multiple-beam interference at the grating and instead diffraction effect would have to be included in the single slit.

The choice of a grating-detector spacing of a few centimeters is also suitable, particularly if all diffraction orders other than those selected for interference were sufficiently far deflected and could in this way be suppressed at the detector. However, if the distance or spacing was in meters, the divergence of the spectral components would resolve the OCT signal.

Reference is specifically made to the discussion provided in DE 10 2004 033 187 B3 according to which expressly the carrier frequency should not be mixed at the difference frequency zero. Thus, in this case admittedly the sought amplitude modulation would be obtained without interference fringes on the line sensor, but the measurable signal would be highly dependent on the phase position of the interference pattern. In the least favourable case during the integrating measurement values relative to the interference signal could cancel one another out over individual pixels. Thus, the effective carrier frequency should be greater than zero and sufficiently small, so that it can be detected without underscanning with the given pixel number according to the Nyquist condition.

For the present invention the exact parallel irradiation of the at least two different diffraction orders on the detector is preferably avoided. This can easily be achieved by a slight variation in the irradiation angle of one of the beams.

In exemplified manner a description is given hereinafter of the design of an OCT detector where the present invention is used. The light source is constituted by a superluminescent diode (SLD) with a central wavelength $\lambda_0$ of 828.3 nm and a bandwidth $\lambda_{SLD\ width}$ of 19.7 nm. The spectral density distribution must be approximatable by a Gaussian function. This also leads to a Gaussian coherence function with a centre-width $l_c$ of 15 μm. For scanning the interference signal use is to be made of a CMOS line sensor. In a $b_{sensor}$=8 mm wide line there are 1024 photodiodes, which gives a pixel or scan spacing $p_{spacing}$ of 7.8 μm. The aim is to obtain a clear depth information from the measured interference signal on the line sensor.

The interference fringes must be reconstructable, i.e. according to the Nyquist criterion the spacing between adjacent interference fringes must be at least twice as large as the scanning spacing (=sensor pixel spacing) pspacing. The angle β to be included by the specimen and reference beam to ensure the avoidance of underscanning is $\beta = \arcsin(\lambda_0/p_{spacing})=3.0°$.

The amplitude modulation to be scanned (the fringe pattern envelope) is formed from Gaussian functions. The Gaussian function with the given half-width must be reconstructable following scanning. For this purpose at least two cosine periods must fit into the half-width of a Gaussian curve. Together with the first criterion it follows that the Gaussian function of at least four pixels must be scanned. For a sensor with 1024 pixels it is possible to achieve a maximum path length difference of $\Delta = 256 \cdot l_c = 3.8$ mm. To achieve this the incidence angle on the grating must be $\alpha = \arctan(\Delta/b_{sensor})=25.4°$.

Corresponding to the now known incidence and emergence angles from the grating, using the grating equation, it is also possible to determine the grating constant, which is $g=(\sin(\alpha)+\sin(\beta))/(m \cdot \lambda)=579$ lines/millimeter.

The invention claimed is:
1. Method for the electronic scanning of the intensity distribution of an optical interference pattern with a linear image sensor, which presets a fixed scanning frequency by its pixel width, the interference pattern resulting from the superimposing of two time partly coherent beams impinging under a random preset angle α with respect to one another and having interference fringes with a carrier frequency higher than the scanning frequency and a slowly variable amplitude modulation with respect to the pixel width, characterized in that an optical grating is so positioned in the optical path of the first of the two impinging beams and the image sensor in the diffraction pattern of the grating that at the position of image sensor at least one beam emanating from the grating in the direction of a secondary diffraction order and the second incident beam not influenced by the grating interfere and the beams include an angle β at the position of the image sensor which is smaller than α.

2. Method according to claim 1, characterized in that the reference beam of an OCT is deflected by the grating.

3. Method according to claim 1, characterized in that an optical phase grating is used.

4. Method according to claim 1, characterized in that grating diffraction takes place by reflection on a grating.

5. Method according to claim 1, characterized in that use is made of broad-band light with short coherence length.

6. Method according to claim 1, characterized in that the image sensor is placed at a distance of at least 1 mm from the grating.

7. Method according to claim 1, characterized in that the beams superimposed on the line sensor include an angle different from zero.

8. Method for the electronic scanning of the intensity distribution of an optical interference pattern with a linear image sensor, which presets a fixed scanning frequency by its pixel width, the interference pattern resulting from the superimposing of two time partly coherent beams impinging under a random preset angle α with respect to one another and having interference fringes with a carrier frequency higher than the scanning frequency and a slowly variable amplitude modulation with respect to the pixel width, characterized in that at least one optical grating is placed in the optical path of both incident beams and the image sensor is placed in the diffraction pattern of the grating in such a way that at the position of the image sensor interference takes place between at least two beams, emanating from the at least one grating, with different diffraction orders of the incident beams, the beams emanating from the at least one grating including an angle β at the position of the image sensor which is smaller than α.

9. Method according to claim 8, characterized in that the reference beam of an OCT is deflected by the grating.

10. Method according to claim 8, characterized in that an optical phase grating is used.

11. Method according to claim 8, characterized in that grating diffraction takes place by reflection on a grating.

12. Method according to claim 8, characterized in that use is made of broad-band light with short coherence length.

13. Method according to claim 8, characterized in that the image sensor is placed at a distance of at least 1 mm from the grating.

14. Method according to claim 8, characterized in that the beams superimposed on the line sensor include an angle different from zero.

* * * * *